(12) United States Patent
Higuchi et al.

(10) Patent No.: US 9,468,418 B2
(45) Date of Patent: Oct. 18, 2016

(54) ULTRASONIC DIAGNOSTIC APPARATUS, ULTRASONIC IMAGE DISPLAY APPARATUS, AND ULTRASONIC IMAGE DISPLAY METHOD

(71) Applicant: TOSHIBA MEDICAL SYSTEMS CORPORATION, Otawara-Shi, Tochigi-Ken (JP)

(72) Inventors: Jiro Higuchi, Otawara (JP); Masato Oonuki, Yaita (JP); Masatoshi Nishino, Otawara (JP); Osamu Nakajima, Otawara (JP); Shinichi Hoshino, Otawara (JP); Tomokazu Fujii, Nasushiobara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 691 days.

(21) Appl. No.: 13/718,296

(22) Filed: Dec. 18, 2012

(65) Prior Publication Data

US 2013/0109970 A1 May 2, 2013

Related U.S. Application Data

(63) Continuation of application No. PCT/JP2012/073601, filed on Sep. 14, 2012.

(30) Foreign Application Priority Data

Sep. 16, 2011 (JP) .................................. 2011-203832
Sep. 12, 2012 (JP) .................................. 2012-200776

(51) Int. Cl.
*A61B 8/14* (2006.01)
*A61B 8/00* (2006.01)
(Continued)

(52) U.S. Cl.
CPC . *A61B 8/14* (2013.01); *A61B 8/00* (2013.01); *A61B 8/06* (2013.01); *A61B 8/0883* (2013.01);
(Continued)

(58) Field of Classification Search
CPC ........ A61B 8/00; A61B 8/06; A61B 8/0883; A61B 8/14; A61B 8/462; A61B 8/463; A61B 8/465; A61B 8/485; A61B 8/488; A61B 8/5207; A61B 8/54
See application file for complete search history.

(56) References Cited

U.S. PATENT DOCUMENTS

2004/0019270 A1 1/2004 Takeuchi
2004/0207661 A1 10/2004 Akaki
(Continued)

FOREIGN PATENT DOCUMENTS

CN 1494873 A 5/2004
CN 1548008 A 11/2004
(Continued)

OTHER PUBLICATIONS

International Search Report (JP) mailed on Dec. 4, 2012 for corresponding International Application No. PCT/JP2012/073601.
(Continued)

*Primary Examiner* — Mark Remaly
(74) *Attorney, Agent, or Firm* — Yoshida & Associates LLC; Kenichiro Yoshida (57) ABSTRACT

According to one embodiment, an internal storage unit stores auxiliary diagnostic indication concerning each of examination items in association with a display position of the auxiliary diagnostic indication in a display area where an ultrasonic image is displayed. An image generation unit generates an ultrasonic image concerning an examination item of a scan target based on an echo signal from an ultrasonic probe. A monitor has a display area. A display control unit controls the monitor so as to display specific auxiliary diagnostic indication, of auxiliary diagnostic indication stored in the storage unit, which is associated with an examination item of the scan target, at a specific display position associated with the specific auxiliary diagnostic indication.

14 Claims, 5 Drawing Sheets

(51) Int. Cl.
    *A61B 8/06*     (2006.01)
    *A61B 8/08*     (2006.01)

(52) U.S. Cl.
    CPC ............... *A61B 8/462* (2013.01); *A61B 8/463* (2013.01); *A61B 8/465* (2013.01); *A61B 8/5207* (2013.01); *A61B 8/54* (2013.01); *A61B 8/485* (2013.01); *A61B 8/488* (2013.01)

(56) References Cited

U.S. PATENT DOCUMENTS

| | | |
|---|---|---|
| 2006/0170714 A1 | 8/2006 | Kanda |
| 2007/0239005 A1* | 10/2007 | Ogasawara .............. A61B 8/14 600/437 |
| 2008/0072674 A1 | 3/2008 | Ume |

FOREIGN PATENT DOCUMENTS

| | | |
|---|---|---|
| CN | 1846630 A | 10/2006 |
| JP | 2001-224596 A | 8/2001 |
| JP | 2001-314399 A | 11/2001 |
| JP | 2003-589 A | 1/2003 |
| JP | 2009-261800 A | 11/2009 |

OTHER PUBLICATIONS

English Translation of International Search Report (JP) mailed on Dec. 4, 2012 for corresponding International Application No. PCT/JP2012/073601.

Chinese Office Action with its English Translation for Chinese Patent Application No. 201280001317.6 mailed on Jun. 18, 2014.

* cited by examiner

| Examination protocol | Auxiliary diagnostic indication candidate | Examination date |
|---|---|---|
| Cardiac ultrasonography | #1 | Examination date: January 20, 2011 |
| | #2 | Examination date: September 5, 2010 |
| | #3 | Examination date: April 14, 2010 |

FIG. 3B

| Examination protocol | Auxiliary diagnostic indication candidate | Examination date |
|---|---|---|
| Cardiac ultrasonography | #1 | Male: Abnormal: Examination date: February 7, 2011 |
| | #2 | Female: Abnormal: Examination date: November 28, 2010 |
| | #3 | Male: Normal: Examination date: January 14, 2011 |

| Examination protocol | Individual examination |
|---|---|
| Cardiac ultrasonography | Apical four-chamber view |
| | Apical long axis view |
| | Apical two-chamber view |
| | Left ventricular long axis view |

F I G. 4

F I G. 5

F I G. 6A

F I G. 6B

ULTRASONIC DIAGNOSTIC APPARATUS, ULTRASONIC IMAGE DISPLAY APPARATUS, AND ULTRASONIC IMAGE DISPLAY METHOD

CROSS REFERENCE TO RELATED APPLICATIONS

This application is a Continuation Application of PCT Application No. PCT/JP2012/073601, filed Sep. 14, 2012 and based upon and claiming the benefit of priority from Japanese Patent Applications No. 2011-203832, filed Sep. 16, 2011; and No. 2012-200776, filed Sep. 12, 2012, the entire contents of all of which are incorporated herein by reference.

FIELD

Embodiments described herein relate generally to an ultrasonic diagnostic apparatus, ultrasonic image display apparatus, and ultrasonic image display method.

BACKGROUND

Ultrasonic diagnostic apparatuses have been used, as medical image diagnostic apparatuses which have merits such as high operability and noninvasiveness (freedom from exposure), for current medical procedures to examine various biological tissues such as the heart, liver, kidneys, and mammary glands.

An ultrasonic diagnostic apparatus transmits ultrasonic waves via an ultrasonic probe and receives ultrasonic waves (reflected waves) reflected by an internal tissue of a subject. The ultrasonic diagnostic apparatus generates ultrasonic images (B-mode images and Doppler images) representing the tissue structure and blood flow information inside a subject based on echo signals from the ultrasonic probe as still images or moving images in chronological order. Generated ultrasonic images are displayed on the monitor and stored in storage media such as IC memories and magnetooptical disks.

In ultrasonic image diagnosis, current and past ultrasonic images concerning the same subject are performed with comparative reading.

On comparative reading, a radiogram radiologist such as a doctor needs to observe a current ultrasonic image as a diagnosis target and a past ultrasonic image as a comparison target. As an ultrasonic image as a comparison target, for example, an ultrasonic image obtained by imaging the same region such as the liver is used. The radiologist uses a body mark as information to search past ultrasonic images for a desired ultrasonic image. A body mark is a schematic view showing the rough contact position and contact direction (in other words, the scanning position and scanning direction) of the ultrasonic probe relative to the subject. The body mark is stored in association with an ultrasonic image.

When displaying a stored past ultrasonic image on the monitor, the ultrasonic diagnostic apparatus also displays the body mark associated with the ultrasonic image. When searching for an ultrasonic image to be used for comparative reading, the radiologist visually perceives the state of a displayed ultrasonic image by referring to the body mark.

Repeated examination is sometimes performed for the same patient (for example, in an obstetrics and gynecology department, the same examination is repeated in chronological order). Alternatively, different subjects are sometimes examined by the same examination protocol. It is necessary to repeatedly input and display auxiliary diagnosis information (a character string, arrow, body mark, probe mark, and the like), which has been displayed on a subject or in an examination in the past, at the same place.

It is an object of the embodiment to provide an ultrasonic diagnostic apparatus, ultrasonic image display apparatus, and ultrasonic image display method, which can reduce the operation load in inputting auxiliary diagnosis information.

DETAILED DESCRIPTION

In general, according to one embodiment, an ultrasonic diagnostic apparatus includes a storage unit, generation unit, a display unit, a control unit. The storage unit stores auxiliary diagnostic indication concerning each of examination items in association with a display position of the auxiliary diagnostic indication in a display area where an ultrasonic image is displayed. The generation unit generates an ultrasonic image concerning a scan target based on an echo signal from an ultrasonic probe. The display unit has a display area for an ultrasonic image. The control unit controls the display unit so as to display specific auxiliary diagnostic indication, of auxiliary diagnostic indication stored in the storage unit, which is associated with an examination item of the scan target at a specific display position associated with the specific auxiliary diagnostic indication.

An ultrasonic diagnostic apparatus, ultrasonic image display apparatus, and ultrasonic image display method according to an embodiment will be described below with reference to the accompanying drawing.

Figure 1:
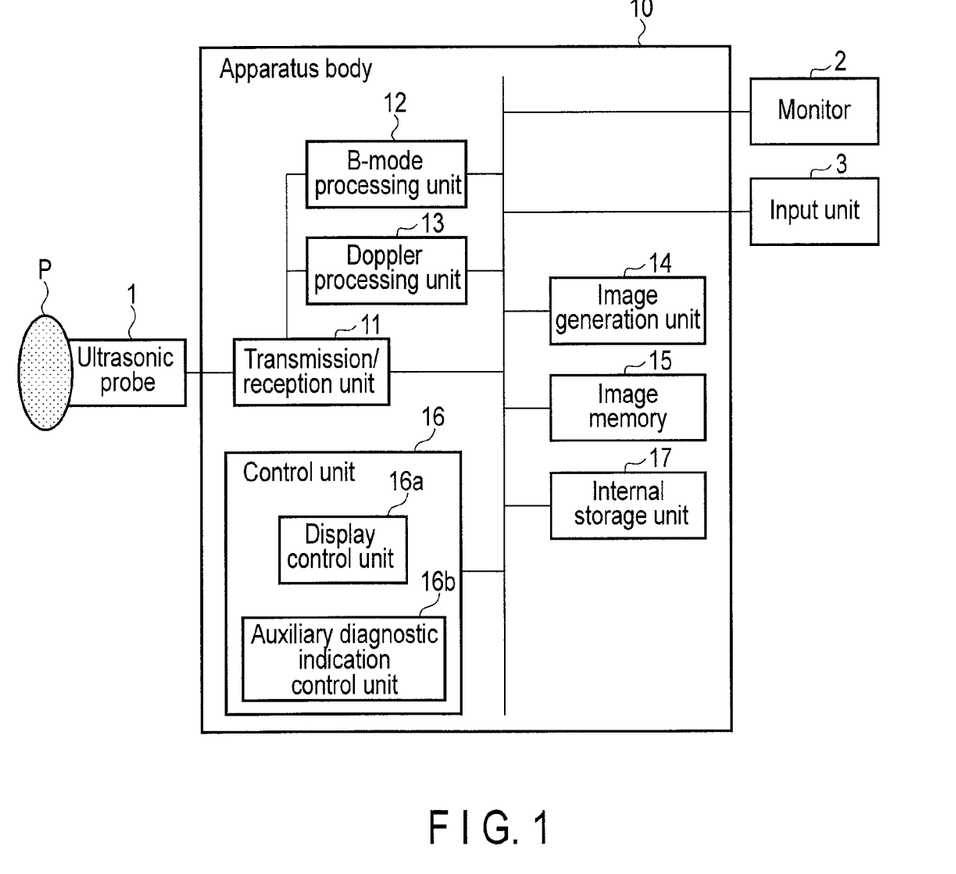
FIG. 1 is a block diagram showing the arrangement of an ultrasonic diagnostic apparatus according to this embodiment.

The arrangement of the ultrasonic diagnostic apparatus according to this embodiment will be described first. FIG. 1 is a block diagram for explaining the arrangement of the ultrasonic diagnostic apparatus according to the embodiment. As shown in FIG. 1, the ultrasonic diagnostic apparatus according to the embodiment includes an ultrasonic probe 1, a monitor (display device) 2, an input unit 3, and an apparatus body 10.

The ultrasonic probe 1 includes piezoelectric transducers. The piezoelectric transducers transmit ultrasonic waves upon reception of driving signals from a transmission/reception unit 11 in the apparatus body 10, receive ultrasonic waves reflected by a subject P, and convert the received ultrasonic waves into an electrical signal. In addition, the ultrasonic probe 1 includes a matching layer provided in front of the piezoelectric transducers and a backing member which prevents ultrasonic waves from propagating backward from the piezoelectric transducers.

When the ultrasonic probe 1 transmits ultrasonic waves to the subject P, the transmitted ultrasonic waves are sequentially reflected by a discontinuity surface of acoustic impedance in an internal tissue of the subject P. The piezoelectric transducers receive the reflected ultrasonic waves as an echo signal. The amplitude of this echo signal depends on an acoustic impedance difference on the discontinuity surface by which ultrasonic waves are reflected. The echo signal produced when ultrasonic waves are reflected by the surface of a moving subject such as a moving blood flow or the cardiac wall is subjected to a frequency shift depending on velocity components in the ultrasonic transmission direction of the moving body due to the Doppler effect.

The ultrasonic probe 1 according to this embodiment may use a two-dimensional scanning scheme and a three-dimensional scanning scheme. In the two-dimensional scanning scheme, the ultrasonic probe 1 incorporates piezoelectric transducers arrayed one-dimensionally and scans a two-dimensional scan plane with an array of piezoelectric transducers. Alternatively, in the two-dimensional scanning scheme, the ultrasonic probe 1 may incorporate piezoelectric transducers arrayed two-dimensionally and scan a two-dimensional scan plane by using a two-dimensional array of piezoelectric transducers. In the three-dimensional scanning scheme according to this embodiment, the ultrasonic probe 1 can use either a mechanical scanning scheme or an electronic scanning scheme. In the mechanical scanning scheme, the ultrasonic probe 1 scans a three-dimensional region by mechanically swinging an array of piezoelectric transducers. In the electronic scanning scheme, the ultrasonic probe 1 scans a three-dimensional region with a two-dimensional array of piezoelectric transducers.

The input unit 3 includes input devices such as a mouse, keyboard, buttons, panel switches, touch command screen, foot switches, and trackball. The input unit 3 accepts various setting requests from the operator of the ultrasonic diagnostic apparatus via input devices and transfers the accepted various setting requests to the apparatus body 10. For example, the input unit 3 accepts an image save request or the like from the operator. The input unit 3 also accepts the input of auxiliary diagnostic indication, as information associated with this embodiment, which is associated with an ultrasonic image. Note that auxiliary diagnostic indication will be described in detail later.

The monitor 2 can display a GUI (Graphical User Interface) with which the operator inputs various kinds of setting requests using the input unit 3. The monitor 2 displays the ultrasonic images generated by the apparatus body 10 and auxiliary diagnostic indication. For example, the monitor 2 displays auxiliary diagnostic indication stored in an internal storage unit 17 (to be described later) or an external storage device in accordance with a request from the operator under the control of an auxiliary diagnostic indication control unit 16b.

The apparatus body 10 functions as the main unit of the ultrasonic diagnostic apparatus. As shown in FIG. 1, the apparatus body 10 includes the transmission/reception unit 11, a B-mode processing unit 12, a Doppler processing unit 13, image generation unit 14, image memory 15, control unit 16, and internal storage unit 17.

The transmission/reception unit 11 supplies driving signals to the ultrasonic probe 1. More specifically, the transmission/reception unit 11 includes a trigger generation circuit, delay circuit, and pulser circuit (none of which are shown) for transmission processing. The pulser circuit repeatedly generates rate pulses for the formation of transmission ultrasonic waves at a predetermined rate frequency fr Hz (period: 1/fr sec). The delay circuit gives each rate pulse a delay time corresponding to a transmission direction and a transmission focal position for each channel. The trigger generation circuit applies a driving signal to the ultrasonic probe 2 at the timing based on this rate pulse. Upon application of a driving signal, the ultrasonic probe 2 transmits an ultrasonic transmission beam in a transmission direction at a transmission focal position in accordance with a delay time. In other words, the delay circuit arbitrarily adjusts a transmission direction from a piezoelectric transducer surface by changing the delay time to be given to each rate pulse.

In addition, the transmission/reception unit 11 generates beam data by performing various types of processing for the echo signal received by the ultrasonic probe 1. More specifically, the transmission/reception unit 11 includes an amplifier circuit, A/D converter, and adder (none of which are shown) for reception processing. The amplifier circuit amplifies an echo signal from the ultrasonic probe 2 for each channel. The A/D converter performs A/D conversion for the amplified echo signal. The adder gives each digital echo signal a delay time necessary to determine the beam direction of an ultrasonic reception beam for each reception focal position, and adds the echo signals given the delay times. Performing this delay addition will enhance each reflection component from a direction corresponding to the reception directivity of the echo signal, thereby generating beam data corresponding to the ultrasonic reception beam.

In this manner, the transmission/reception unit 11 controls the transmission directivity and the reception directivity in ultrasonic transmission/reception. Note that the transmission/reception unit 11 has a function capable of instantaneously changing delay information, transmission frequency, transmission driving voltage, the number of piezoelectric transducers included in the aperture, and the like under the control of the control unit 16 (to be described later). The transmission/reception unit 11 can also transmit and receive different waveforms for each frame or rate.

The B-mode processing unit 12 performs logarithmic amplification, envelope detection processing, and the like for beam data from the transmission/reception unit 11 to generate B-mode data whose signal intensity is expressed by a brightness level.

The Doppler processing unit 13 performs frequency analysis for beam data from the transmission/reception unit 11 to extract a blood flow, tissue, contrast medium echo component due to the Doppler effect, thereby generating Doppler data which expresses moving body information such as an average velocity, variance, or power in color.

The image generation unit 14 generates a B-mode image expressing the intensity of a reflected wave by brightness in real time based on B-mode data from the B-mode processing unit 12, and generates a Doppler image expressing moving body information by color in real time based on Doppler data from the Doppler processing unit 13. As a Doppler image, the image generation unit 14 can generate, for example, an average velocity image, variance image, or power image. B-mode images and Doppler images will be collectively referred to as ultrasonic images hereinafter.

The image memory 15 is a memory which stores ultrasonic images from the image generation unit 14. The image memory 15 may be one or both of another storage device connected via a network (not shown) and the above memory.

The internal storage unit 17 stores various types of data such as control programs for performing ultrasonic transmission/reception, image processing, and display processing, diagnostic information, and examination protocols. The internal storage unit 17 is also used to archive images stored in the image memory 15, as needed. Note that the data stored in the internal storage unit 17 can be transferred to an external peripheral apparatus via an interface circuit (not shown).

The internal storage unit 17 stores, for each of examination items, auxiliary diagnostic indication in association with the display position of the auxiliary diagnostic indication in the display area where an ultrasonic image is displayed. Auxiliary diagnostic indication is display information to be added to an ultrasonic image by the operator via the input unit 3 at the time of observation of the ultrasonic image. More specifically, display information to be actually displayed as auxiliary diagnostic indication includes at least one of a mark, graphic pattern, character, and symbol. Marks include, for example, a body mark and a probe mark. A body mark or a probe mark is a schematic view showing the rough contact position and contact direction of the ultrasonic probe relative to the subject at the time of ultrasonic scanning. Alternatively, auxiliary diagnostic indication may be a character string, graphic pattern, or symbol which indicates an examination time, a scan region, or the position of a scan region. A character string, graphic pattern, or symbol indicating the position of a scan region will be referred to as observation location indication. In addition, as auxiliary diagnostic indication, it is possible to use a character string, mark, or graphic pattern representing a measurement result. Note that auxiliary diagnostic indication may be an arbitrary character string, arrow, or the like input by the operator using the keyboard or the like. An examination item includes at least one of a scan region, imaging mode, and display condition. Scan regions used for examination items include all observation targets for ultrasonic examinations such as the heart, liver, stomach, lower abdomen, neck region, and fetus. As imaging modes used for examination items, there are known a B mode, Doppler mode, elastography mode, shear wave elastography mode, and WMT (wall motion tracking) mode. Display conditions used for examination items include a visual field depth (depth) and a gain. The internal storage unit 17 may store auxiliary diagnostic indication in association with patient information, operator information, examination dates, and the like. Patient information and operator information include names and IDs. The display position of auxiliary diagnostic indication in the display area where an ultrasonic image is displayed is specifically the display coordinates of the auxiliary diagnostic indication on the ultrasonic image.

Note that auxiliary diagnostic indication may be registered as default information in advance or may be newly registered by the operator via the input unit 3. The internal storage unit 17 may also store the auxiliary diagnostic indication received from an external apparatus via a network, and may further temporarily store the auxiliary diagnostic indication extracted from a past ultrasonic image of the subject which is to receive an examination. The internal storage unit 17 also stores auxiliary diagnostic indication corresponding to an examination protocol in the same manner.

An examination protocol indicates a series of examination including scanning on one or a plurality of scan regions. This examination protocol can be rephrased as an examination procedure. Examination protocols include, for example, heart screening, upper abdomen screening, and blood vessel screening. Heart screening is a series of examination including examination items such as a left sternal border long axis examination, left sternal border short axis examination, apical long axis examination, and apical four-chamber view examination. In a left sternal border long axis examination, for example, the operator makes the ultrasonic probe 1 approach the following regions from the third and fourth intercostal space at the left sternal border to observe them: the positions and wall motions of the aorta (AO), left atrium (LA), and left ventricle (LV) and the states of the anterior mitral leaflet (AML) of the mitral valve (MV), posterior mitral leaflet (PML), and aortic valve (AV). When performing a left sternal border short axis examination, the operator, for example, rotates the ultrasonic probe 1 clockwise through 90° from a left sternal border long axis view. An apical long axis examination is used to diagnose anteroseptal and posterior wall ischemic diseases with a left ventricular long axis view including the cardiac apex which cannot be approached by a left sternal border long axis view. This examination is also suitable for the observation of a left ventricular inflow waveform and a stricture region blood flow by using the Doppler method. In an apical four-chamber view examination, the operator observes the motions of the septum and side wall, mitral valve, and tricuspid valve by simultaneously visualizing the left and right cardiac chambers with the tomographic image obtained by rotating the ultrasonic probe 1 clockwise through 90° from the apical long axis view. Using such an examination protocol will generate ultrasonic images concerning the respective examination items.

An examination corresponding to each examination item included in an examination protocol will be referred to as an individual examination hereafter. In this individual examination, scanning a target scan region will generate an ultrasonic image concerning the target scan region.

Individual examinations included in an examination protocol will be described in a predetermined order. Auxiliary diagnostic indication is associated with each individual examination.

The control unit 16 controls each unit of the ultrasonic diagnostic apparatus. More specifically, the control unit 16 controls ultrasonic image generation processing by controlling the transmission/reception unit 11, the B-mode processing unit 12, the Doppler processing unit 13, and the image generation unit 14 based on various setting requests input from the operator via the input unit 3 and various control programs read from the internal storage unit 17.

As shown in FIG. 1, the control unit 16 includes a display control unit 16a and the auxiliary diagnostic indication control unit 16b. The display control unit 16a controls the monitor 2 to display various kinds of information in the display area provided on the monitor 2. For example, the display control unit 16a displays the ultrasonic image generated by the image generation unit 14 on the monitor 2 in real time. The display control unit 16a reads out an ultrasonic image stored in the image memory 15 or the internal storage unit 17 and displays the readout ultrasonic image on the monitor 2.

For example, the display control unit 16a reads out, from the internal storage unit 17, an ultrasonic image selected by the operator from the ultrasonic images stored in the internal storage unit 17, and displays the selected ultrasonic image on the monitor 2 upon acceptance of a request to display the selected ultrasonic image, which is issued via the input unit 3.

Requests to display ultrasonic images include, for example, a request to sequentially display the ultrasonic images generated by the image generation unit 14 and stored in the image memory 15 or the internal storage unit 17 and a request to display an ultrasonic image selected from the ultrasonic images generated in the past by the image generation unit 14 and stored in the internal storage unit 17 or an external storage device, in order to display ultrasonic images concerning internal tissue of the subject during scanning in real time.

The display control unit 16a also controls the monitor 2 so as to display specific auxiliary diagnostic indication, of the auxiliary diagnostic indication stored in the internal storage unit 17, which is associated with an examination item of a scan target, at a specific display position associated with the specific auxiliary diagnostic indication in accordance with an instruction from the auxiliary diagnostic indication control unit 16b. The display timing of auxiliary diagnostic indication associated with an examination item of a scan target may be before or during the display of the ultrasonic image concerning the examination item of the scan target. If the display timing is during the display of the ultrasonic image concerning the examination item of the scan target, the auxiliary diagnostic indication is superimposed and displayed on the ultrasonic image concerning the examination item of the scan target. If the display timing is before the display of the ultrasonic image concerning the examination item of the scan target, the auxiliary diagnostic indication is displayed singly. The operator selects an examination item of a scan target via, for example, the input unit 3. When the apparatus executes an examination protocol, the auxiliary diagnostic indication control unit 16 automatically selects an examination item from individual examinations included in the examination protocol in accordance with an examination order. In this case, the display control unit 16a preferably displays auxiliary diagnostic indication before the execution of the individual examination.

If auxiliary diagnostic indication is associated with an ultrasonic image, the display control unit 16a displays the auxiliary diagnostic indication together with the ultrasonic image or displays only the ultrasonic image upon removing the auxiliary diagnostic indication from the display area under the control of the auxiliary diagnostic indication control unit 16b.

When the operator selects an examination protocol and inputs an examination start instruction via the input unit 3, the display control unit 16a displays only the auxiliary diagnostic indication associated with the individual examination in advance on the monitor 2 in accordance with the order of the individual examinations.

More specifically, the display control unit 16a displays the same past examination protocol as that for the subject to be examined or thumbnails or a list of the same past examination protocols as those for other subjects. Alternatively, the display control unit 16a displays the examination protocol registered in advance in the internal storage unit 17 or an external storage device (not shown) on a network. When the apparatus is to perform an examination in accordance with an invoked examination protocol, the auxiliary diagnostic indication control unit 16b instructs the display control unit 16a to display observation location indication concerning a scan region in the first individual examination on the monitor 2.

The auxiliary diagnostic indication control unit 16b issues, to the display control unit 16a, an instruction to display auxiliary diagnostic indication stored in the internal storage unit 17 or an external storage device, together with an ultrasonic image. More specifically, the auxiliary diagnostic indication control unit 16b instructs the display control unit 16a to display auxiliary diagnostic indication, of the auxiliary diagnostic indication added to the ultrasonic image, which is designated via the input unit 3, on the monitor 2. For example, the auxiliary diagnostic indication control unit 16b issues an instruction to display only observation location indication, only a marker indicating a tumor or a region of interest, or only the character string input by the operator or select and display a combination of them. The auxiliary diagnostic indication control unit 16b also reads out the display position associated with auxiliary diagnostic indication and instructs the display control unit 16a so as to display the information on the monitor actually used for diagnosis in conformity with the image size.

Figure 2:
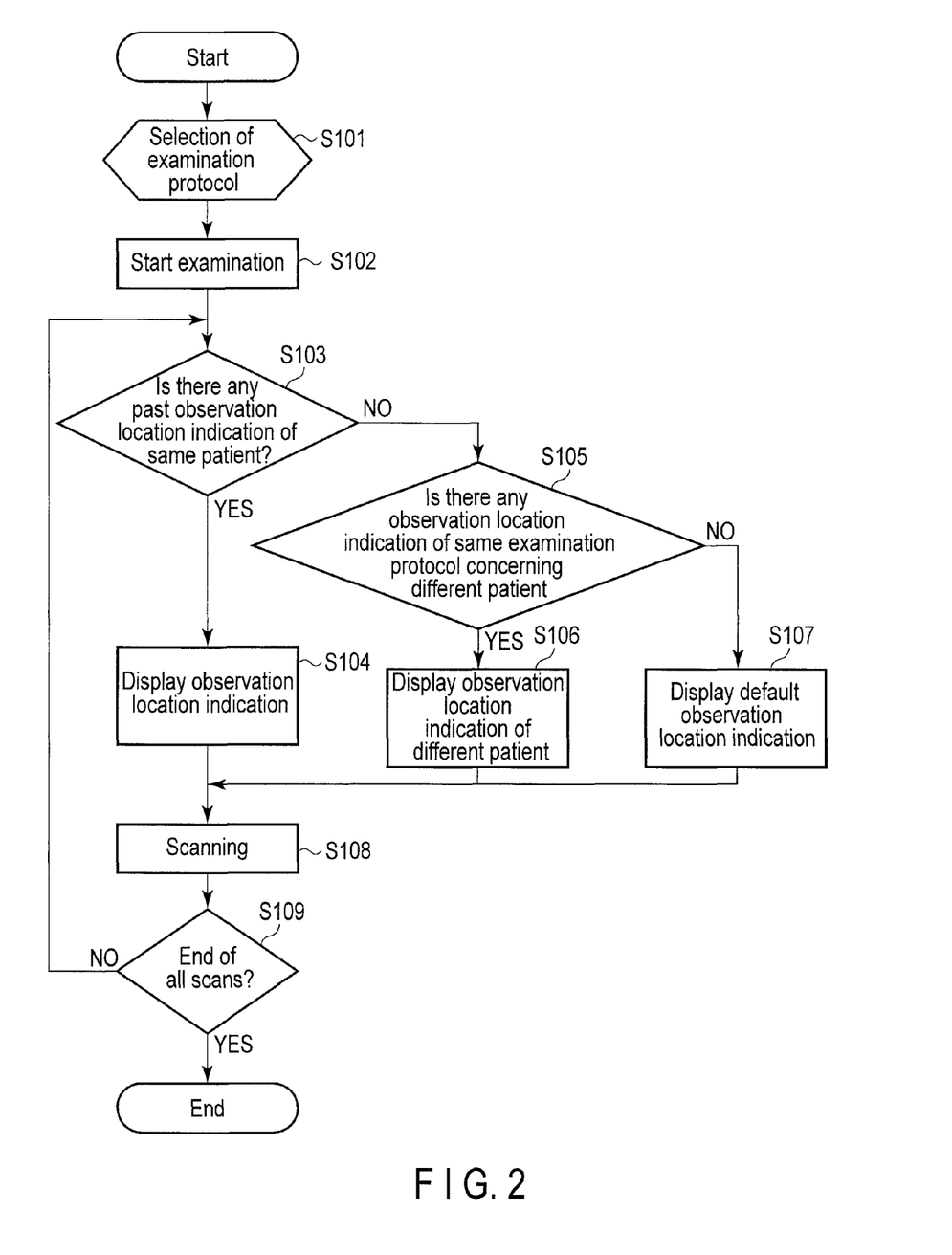
FIG. 2 is a flowchart showing an example of an examination procedure by the ultrasonic diagnostic apparatus according to this embodiment.
Figure 3A:
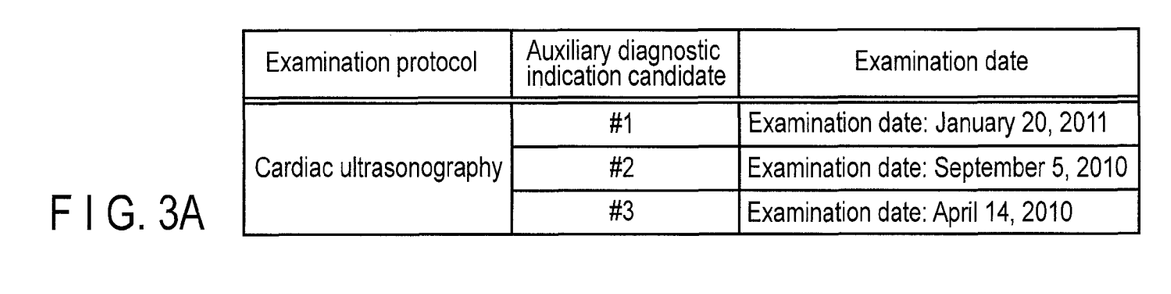
FIG. 3A is a view showing an example of display of diagnostic region indication candidates of the same patient in an examination protocol according to this embodiment.
Figure 3B:
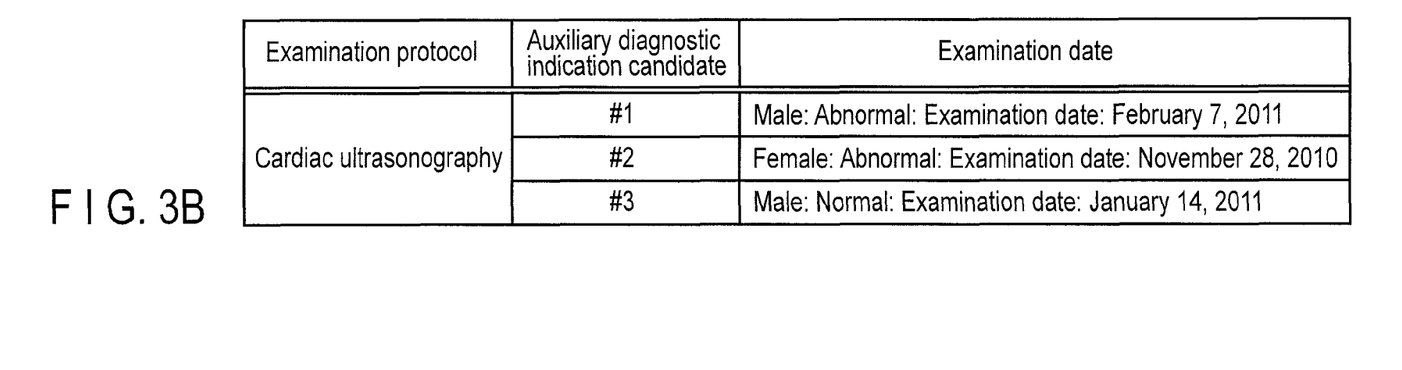
FIG. 3B is a view showing an example of display of past diagnostic region indication candidates in an examination protocol according to this embodiment.
Figure 4:
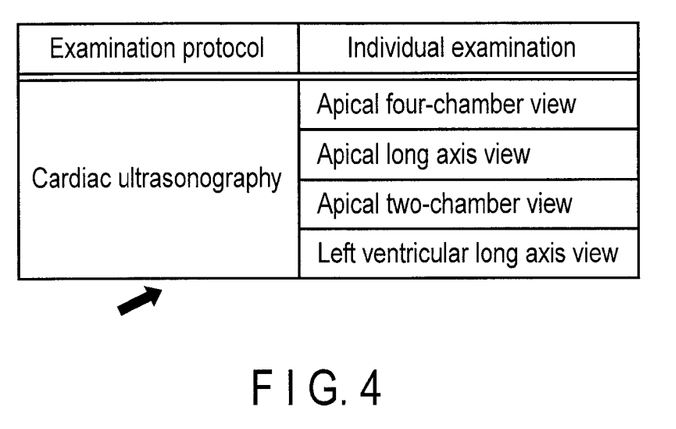
FIG. 4 is a view showing an example of the details of individual examinations in an examination protocol according to this embodiment.
Figure 5:
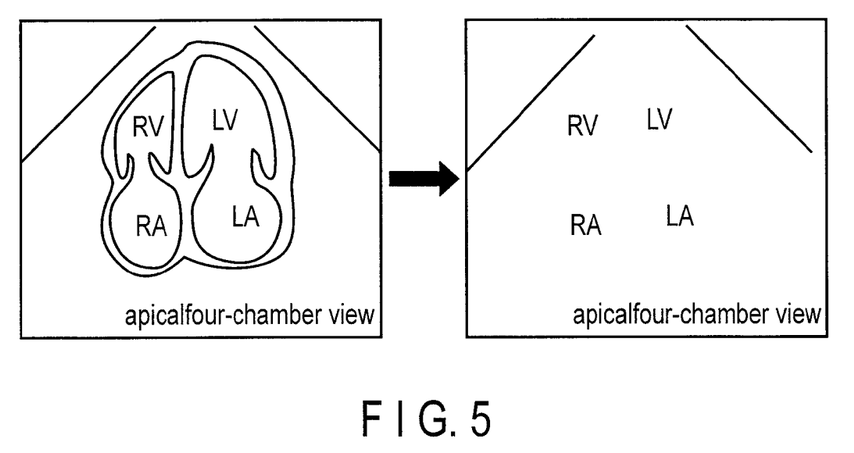
FIG. 5 is a view showing an example of display of diagnostic region indication according to this embodiment.
Figure 6A:
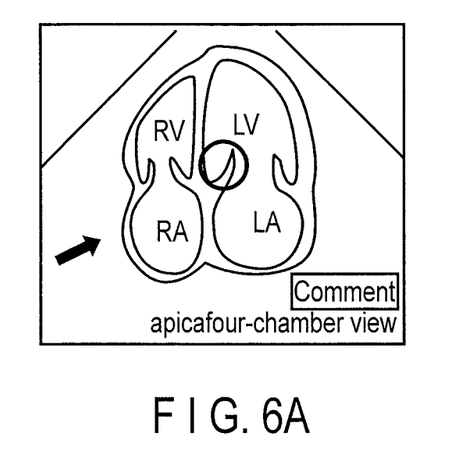
FIG. 6A is a view showing an example of display in which auxiliary diagnostic indication is superimposed on an ultrasonic image according to this embodiment.
Figure 6B:
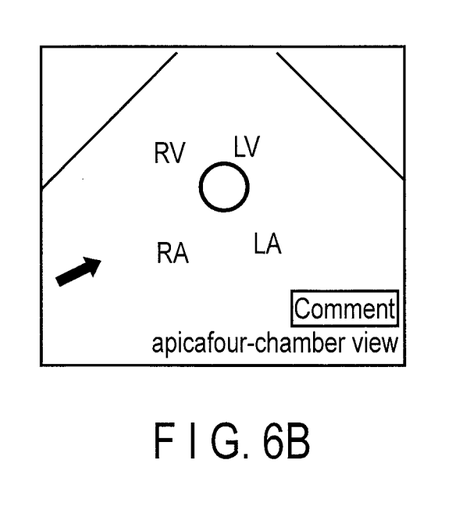
FIG. 6B is a view showing an example of display of auxiliary diagnostic indication in FIG. 6A.

An example of the operation of the ultrasonic diagnostic apparatus according to this embodiment will be described next with reference to FIGS. 1, 2, 3A, 3B, 4, 5, 6A, and 6B. FIG. 2 is a flowchart showing an example of a procedure for the operation of the ultrasonic diagnostic apparatus according to this embodiment, which is performed under the control of the control unit 16. FIG. 3A shows an example of display of auxiliary diagnostic indication candidates of the same patient in an examination protocol according to the embodiment. FIG. 3B shows an example of display of past auxiliary diagnostic indication candidates in the examination protocol according to the embodiment. FIG. 4 shows an example of the details of individual examinations in the examination protocol according to the embodiment. FIG. 5 shows an example of display of auxiliary diagnostic indication according to the embodiment. FIG. 6A shows an example of display in which auxiliary diagnostic indication is superimposed on an ultrasonic image according to this embodiment. FIG. 6B is a view showing an example of display of auxiliary diagnostic indication in FIG. 6A. Note that the following will exemplify a case in which the operator of the ultrasonic diagnostic apparatus has selected one examination protocol from examination protocols for the same examination (e.g., heart screening).

Assuming that auxiliary diagnostic indication is observation location indication, the following description will exemplify a case in which the observation location indication is displayed on the monitor 2. Auxiliary diagnostic indication of a display target may be selected in advance by the operator via the input unit 3 or may be changed after the start of scanning. For example, it is possible to switch between displaying and not displaying auxiliary diagnostic indication by turning on and off the corresponding check box. Displaying necessary auxiliary diagnostic indication in a limited way in this manner will improve readability on the screen and facilitate an examination process. In addition, as shown in FIG. 6B, the display control unit 16a can also display notes of previous findings to allow the operator to intensively check a region of interest in the current scanning. For example, as shown in FIG. 6B, the display control unit 16a displays a frame border or the like enclosing notes of findings or a region of interest. If notes of findings interfere with the observation of an ultrasonic image or the like, the operator can erase the notes from the display area.

In this embodiment, as shown in FIG. 2, the display control unit 16a displays at least one of examination protocols on the monitor 2 in accordance with examination information such as a patient ID and an examination type input in advance via a network or input via the input unit 3. The operator selects a protocol to be actually used for the execution of an examination from the examination protocols displayed on the monitor 2 via the input unit 3 (step S101). Note that if one examination protocol is displayed, the examination protocol may be selected by the operator via the input unit 3 or may not be selected. If the examination protocol is not selected, the control unit 16 automatically starts an examination. Alternatively, as shown in FIG. 4, the display control unit 16a may display a list of selected examination protocols and rearrange examination items. The rearranged examination protocols are stored in the internal storage unit 17 or an external storage device.

When the apparatus starts an examination according to the set examination protocol (step S102), the auxiliary diagnostic indication control unit 16b checks whether the same past observation location indication as that in the same examination protocol as that for the same patient is recorded in the internal storage unit 17 or an external storage device (step S103). If there is the same past observation location indication as that in the same examination protocol, the display control unit 16a displays a list of identifiers of these observation location indications as shown in, for example, FIG. 3A. Note that the display control unit 16a may display thumbnails like display models as observation location indication instead of identifier. If there are observation location indications, the display control unit 16a may display observation location indications in a candidate order complying with a predetermined condition, as shown in FIG. 3A. In the case shown in FIG. 3A, observation location indication whose examination date is nearest to the current examination is displayed as the first candidate. In other words, observation location indications are displayed from the latest ones. However, observation location indications may be displayed from the oldest ones. It is also possible to decide the order of candidates depending on whether there are notes of findings. In this case, the display control unit 16a may display observation location indication with which notes of findings are associated preferentially over other observation location indication in terms of the order of candidates. Note that it is preferable to allow the operator to select a candidate order rule by using the input unit 3.

The display control unit 16a displays the selected observation location indication on the monitor 2 (step S104). Note that the display control unit 16a may initially display observation location indication together with an associated ultrasonic image, as shown in FIG. 5. In this case, the display control unit 16a may automatically erase only the ultrasonic image from the display area on the monitor 2 after the lapse of a predetermined period of time since the display time of the ultrasonic image and the observation location indication. In this case, the display control unit 16a displays the observation location indication in the display area. Note that the ultrasonic image may be erased from the display area upon input of an instruction by the operator via the input unit 3 instead of being automatically erased after the lapse of a predetermined period of time in the above manner. The display control unit 16a may initially display only the observation location indication instead of initially displaying the observation location indication and the ultrasonic image. Alternatively, as shown in FIG. 5, the display control unit 16a may display auxiliary diagnostic indication representing a general term (e.g., Apical four-chamber view) of an image to be acquired, together with observation location indication. Note that these indications may be stored in advance together with ultrasonic images.

If the magnification of diagnostic region indication as a display target differs from the display magnification of an ultrasonic image to be acquired, the display control unit 16a can display auxiliary diagnostic indication of a display target at the same anatomical region in accordance with the display position (coordinates) associated with the auxiliary diagnostic indication.

If there are observation location indications corresponding to a different examination order of the same individual examinations, the display control unit 16a may display the observation location indication upon rearranging the observation order of the individual examinations in the current examination protocol.

If there is no same past observation location indication as that of the same patient in step S103, the display control unit 16a checks whether the internal storage unit 17 or an external storage device stores observation location indication based on the same examination protocol on other patients (step S105). If there is no observation location indication based on the same examination protocol on other patients, the display control unit 16a displays default observation location indication stored in the internal storage unit 17 or an external storage device on the monitor 2 (step S107).

The display control unit 16a may initially display observation location indication together with an associated ultrasonic image, as shown in FIG. 5. In this case, the display control unit 16a may automatically erase only the ultrasonic image from the display area on the monitor 2 after the lapse of a predetermined period of time since the display time of the ultrasonic image and the observation location indication. In this case, the display control unit 16a displays the observation location indication in the display area. Note that the ultrasonic image may be erased from the display area upon input of an instruction by the operator via the input unit 3 instead of being automatically erased after the lapse of a predetermined period of time in the above manner. The display control unit 16a may initially display only the observation location indication instead of initially displaying the observation location indication and the ultrasonic image.

Note that the internal storage unit 17 stores default observation location indications in association with the respective examination items. In this case, the auxiliary diagnostic indication control unit 16b selects optimal default observation location indication from default observation location indications in accordance with the physical information of a subject. The physical information includes, for example, the physique, age, and sex of the subject. The internal storage unit 17 stores the physical information in association with default observation location indication. For example, the auxiliary diagnostic indication control unit 16b selects observation location indication associated with the same physical information as that of the subject from default observation location indications. The display control unit 16a displays the selected default observation location indication on the monitor 2. Displaying the optimal observation location indication for the physical information of the subject allows the operator to easily adjust the contact position, contact direction, and the like of the ultrasonic probe 1 at the time of scanning.

If observation location indications of different patients concerning the same examination protocol are stored, for example, the display control unit 16a displays the observation location indications of the different patients, as shown in FIG. 3B.

The display control unit 16a displays the observation location indications of other patients concerning the same examination protocol on the monitor 2 (step S106). Note that the display control unit 16a may initially display observation location indication together with an associated ultrasonic image, as shown in FIG. 5. In this case, the display control unit 16a may automatically erase only the ultrasonic image from the display area of the monitor 2 after the lapse of a predetermined period of time since the display time of the ultrasonic image and the observation location indication. In this case, the observation location indication is displayed in the display area. Note that the ultrasonic image may be erased from the display area upon input of an instruction by the operator via the input unit 3 instead of being automatically erased after the lapse of a predetermined period of time in the above manner. The display control unit 16a may initially display only the observation location indication instead of initially displaying the observation location indication and the ultrasonic image.

When the observation location indication is displayed (step S04, S106, or S107), the transmission/reception unit 11 scans the scan region (step S108). The image generation unit 14 generates an ultrasonic image based on echo signals from the ultrasonic probe. Observation location indication is displayed for each individual examination before an ultrasonic image in accordance with an instruction from the operator via the input unit 3. Thereafter, an ultrasonic image concerning the individual examination is acquired and displayed. Displaying the observation location indication before scanning allows the operator to easily perceive the angle and place of the ultrasonic probe 1 at which it comes into contact with the subject. This can prevent the operator from scanning a wrong portion or leaving unscanned portions. When scanning in all the individual examinations is complete, the control unit 16 terminates the examination (step S109).

When superimposing and displaying observation location indication on an ultrasonic image, the apparatus may display the observation location indication at an anatomically inappropriate position. In this case, the display control unit 16a may change the display position of the observation location indication or add new observation location indication to the ultrasonic image in accordance with an instruction from the operator via the input unit 3. In addition, the apparatus may store auxiliary diagnostic indication and an ultrasonic image in different layers in the internal storage unit 17. In this case, the display control unit 16a can display the auxiliary diagnostic indication and the ultrasonic image separately on the monitor 2. For example, the display control unit 16a can display only the auxiliary diagnostic indication on the monitor 2.

For example, as shown in FIG. 6A, the display control unit 16a may superimpose the respective auxiliary diagnostic indications such as a frame border enclosing a region of interest, arrow, and comment on an ultrasonic image. Alternatively, as shown in FIG. 6B, the display control unit 16a may display only auxiliary diagnostic indication. Note that the respective auxiliary diagnostic indication such as a frame border enclosing a region of interest, arrow, and comment are stored in different layers in the internal storage unit 17. The auxiliary diagnostic indication control unit 16b can separately switch between displaying and not displaying each auxiliary diagnostic indication in accordance with an instruction from the operator via the input unit 3. This allows the operator to selectively display only truly necessary information, and hence can further improve the examination efficiency.

As described above, the ultrasonic diagnostic apparatus according to this embodiment includes the internal storage unit 17, the image generation unit 14, the monitor 2, and the display control unit 16a. The internal storage unit 17 stores auxiliary diagnostic indication concerning each of examination items in association with the display position of each auxiliary diagnostic indication in the display area. The image generation unit 14 generates an ultrasonic image concerning an examination item of a scan target based on an echo signal from the ultrasonic probe 1. The monitor 2 has a display area. The display control unit 16a controls the monitor 2 so as to display auxiliary diagnostic indication, of the auxiliary diagnostic indication stored in the internal storage unit 17, which is associated with an examination item of a scan target at a specific display position, in the display area of the monitor 2, which is associated with specific auxiliary diagnostic indication.

With this arrangement, the ultrasonic diagnostic apparatus according to this embodiment can reuse preregistered auxiliary diagnostic indication for the current examination. The ultrasonic diagnostic apparatus according to this embodiment can display the auxiliary diagnostic indication registered in advance concerning the examination item on the monitor 2 before display of an ultrasonic image concerning the examination item of the scan target. The operator therefore need not add any auxiliary diagnostic indication to an ultrasonic image for each examination from the beginning. This can save the trouble of inputting auxiliary diagnostic indication. When performing examinations on examination items, the ultrasonic diagnostic apparatus according to this embodiment displays preregistered auxiliary diagnostic indication on the monitor 2 before display of an ultrasonic concerning each examination item. This makes it easy for the operator to visually recognize the examination order of examination items, and makes it difficult for examination omissions to occur.

In addition, according to this embodiment, displaying auxiliary diagnostic indication of an ultrasonic image concerning examination items allows the operator to perform an examination while perceiving the position of previous findings, and hence can shorten the time.

According to this embodiment, it is possible to reduce the operation load in inputting auxiliary diagnostic indication.

Note that the above description has exemplified the ultrasonic diagnostic apparatus as this embodiment. However, an apparatus which implements the embodiment is not limited to an ultrasonic diagnostic apparatus. For example, the apparatus body 10 in FIG. 1 may be an ultrasonic image display apparatus such as a workstation separate from an ultrasonic diagnostic apparatus. This ultrasonic image display apparatus is connected to, for example, an ultrasonic diagnostic apparatus via a network, and hence can receive the ultrasonic images generated by the ultrasonic diagnostic apparatus via the network. This allows the ultrasonic image display apparatus according to this embodiment to perform the same processing as that performed by the ultrasonic diagnostic apparatus according to the embodiment described above.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an internal storage configured to store auxiliary diagnostic indication concerning each of examination items in association with a display position of the auxiliary diagnostic indication in a display area where an ultrasonic image is displayed;
a monitor configured to have a display area for an ultrasonic image; and
controller
configured to generate an ultrasonic image concerning a scan target based on an echo signal from an ultrasonic probe, and
control the monitor so as to display specific auxiliary diagnostic indication, of auxiliary diagnostic indication stored in the internal storage, which is associated with an examination item of the scan target at a specific display position associated with the specific auxiliary diagnostic indication.

2. The ultrasonic diagnostic apparatus of claim 1, wherein the controller configured to display the specific auxiliary diagnostic indication at the specific display position before display of the generated ultrasonic image.

3. The ultrasonic diagnostic apparatus of claim 1, wherein the monitor displays the generated ultrasonic image in the display area in real time, and
the controller superimposes the specific auxiliary diagnostic indication on the generated ultrasonic image.

4. The ultrasonic diagnostic apparatus of claim 1, wherein an examination item of the scan target includes sub-examination items included in an examination protocol, and
the controller controls the monitor so as to display the specific auxiliary diagnostic indication associated with each of the sub-examination items at a display position associated with the specific auxiliary diagnostic indication in an order corresponding to an examination order of the sub-examination items.

5. The ultrasonic diagnostic apparatus of claim 1, wherein the examination item includes at least one of a scan region, an imaging mode, and a display condition.

6. The ultrasonic diagnostic apparatus of claim 1, wherein the internal storage stores the auxiliary diagnostic indication in association with at least one of operator information and patient information.

7. The ultrasonic diagnostic apparatus of claim 1, wherein the auxiliary diagnostic indication includes at least one of a mark, a graphic pattern, a character, and a symbol.

8. The ultrasonic diagnostic apparatus of claim 1, wherein the specific auxiliary diagnostic indication includes auxiliary diagnostic indications, and
the controller configured to display the auxiliary diagnostic indication based on at least one of a physique, age, and sex of a subject.

9. The ultrasonic diagnostic apparatus of claim 1, the controller further configured to automatically select an examination item of the scan target in accordance with an instruction from a user or an examination protocol.

10. The ultrasonic diagnostic apparatus of claim 1, further comprising an input unit configured to add auxiliary diagnostic indication to an ultrasonic image displayed by the monitor in accordance with an instruction from a user, and
the internal storage stores auxiliary diagnostic indication added via the input unit, a display position of the added auxiliary diagnostic indication, and the displayed ultrasonic image in association with each other.

11. The ultrasonic diagnostic apparatus of claim 1, wherein the auxiliary diagnostic indication is stored in association with an ultrasonic image generated concerning each of the examination items.

12. The ultrasonic diagnostic apparatus of claim 1, wherein the auxiliary diagnostic indication is stored together with an ultrasonic concerning each of past examination items of the subject.

13. The ultrasonic diagnostic apparatus of claim 1, wherein the auxiliary diagnostic indication includes observation location indication.

14. An ultrasonic image display apparatus comprising:
an internal storage configured to store auxiliary diagnostic indication concerning each of examination items in association with a display position of the auxiliary diagnostic indication in a display area where an ultrasonic image is displayed;
a monitor configured to have a display area for an ultrasonic image; and
controller
configured to control the monitor so as to display specific auxiliary diagnostic indication, of auxiliary diagnostic indication stored in the internal storage, which is associated with an examination item of the scan target, at a specific display position associated with the specific auxiliary diagnostic indication.

* * * * *